United States Patent [19]

Bischoff et al.

[11] Patent Number: 5,705,342

[45] Date of Patent: Jan. 6, 1998

[54] INTERACTION OF BCL-2 AND R-RAS

[75] Inventors: James R. Bischoff; Maria Jose Fernandez-Sarabia, both of Kensington, Calif.

[73] Assignee: Onyx Pharmaceuticals, Inc., Richmond, Calif.

[21] Appl. No.: 484,945

[22] Filed: Jun. 7, 1995

Related U.S. Application Data

[63] Continuation of Ser. No. 110,287, Aug. 20, 1993, Pat. No. 5,539,085.

[51] Int. Cl.$^6$ .................. G01N 33/53; C12Q 1/68
[52] U.S. Cl. .................. 435/6; 435/71; 435/7.21; 435/723; 435/724; 435/375
[58] Field of Search .................. 530/350; 435/4, 435/7.93, 7.1, 7.21, 7.23, 7.24, 367, 375, 6; 424/193.1

[56] References Cited

U.S. PATENT DOCUMENTS 5,550,019  8/1996  Reed .................. 435/6

OTHER PUBLICATIONS

Reed et al., Molecular and Cellular Biology, vol. 10, pp. 4370–4374, 1990.

Lowe et al., Cell, vol. 48, pp. 137–146, 1987.

Chien et al., PNAS, vol. 88, pp. 9578–9582, 1991.

*Primary Examiner*—James Ketter
*Assistant Examiner*—Iven Yucel
*Attorney, Agent, or Firm*—Gregory Giotta; Melya J. Hughes; Richard L. Neeley

[57] ABSTRACT

The invention provides compositions and methods for screening for agents which are modulators of bcl-2 function and can modulate bcl-2-mediated apoptosis and/or modulate neoplastic and immune conditions dependent upon bcl-2 function. The invention also provides a composition comprising a substantially pure protein complex comprising a R-ras polypeptide and a bcl-2 polypeptide.

10 Claims, 3 Drawing Sheets

INTERACTION OF BCL-2 AND R-RAS

CROSS REFERENCE TO RELATED APPLICATIONS

This application is a continuation of U.S. application Ser. No. 08/110,287, filed Aug. 20, 1993, now U.S. Pat. No. 5,539,085.

TECHNICAL FIELD

The invention provides compositions comprising substantially purified complexes comprising R-ras and bcl-2 polypeptides; methods for detecting complexes formed by intermolecular association between an R-ras polypeptide and a bcl-2 polypeptide; methods for identifying agents which inhibit formation of complexes comprising R-ras and bcl-2; methods for modulating cell proliferation, cell differentiation, and cell apoptosis by administering an agent that alters formation and/or activity of complexes comprising R-ras and bcl-2; and methods of treating a pathological condition by administering an agent that alters formation and/or activity of complexes comprising R-ras and bcl-2.

BACKGROUND

Apoptosis is a term used to refer to the process(es) of programmed cell death and has been described in several cell types (Waring et al. (1991) *Med. Res. Rev.* 11: 219; Williams G T (1991) *Cell* 65: 1097; Williams G T (1992) *Trends Cell Biol.* 2: 263; Yonisch-Rouach et al. (1991) *Nature* 352: 345). Apoptosis is likely involved in controlling the amount and distribution of certain differentiated cell types, such as lymphocytes and other cells of the hematopoietic lineage. The mechanism(s) by which apoptosis is produced in cells is incompletely understood, as are the regulatory pathways by which the induction of apoptosis occurs.

bcl-2

The protein encoded by the bcl-2 proto-oncogene has been reported to be capable of inhibiting apoptosis in many hematopoietic cell systems. The proto-oncogene bcl-2 was isolated and characterized as a result of its frequent translocation adjacent to the immunoglobulin heavy chain enhancer in the t(14;18) chromosome translocation present in more than 80% of human follicular lymphomas (Chen-Levy et al. (1989) *Mol. Cell. Biol.* 9: 701; Cleary et al. (1986) *Cell* 47: 19). These neoplasias are characterized by an accumulation of mature resting B cells presumed to result from a block of apoptosis which would normally cause turnover of these cells. Transgenic mice expressing bcl-2 under the control of the Eµ enhancer similarly develop follicular lymphomas which have a high incidence of developing into malignant lymphomas (Hockenberry et al. (1990) *Nature* 348: 334; McDonnell T J and Korsmeyer S J (1991) *Nature* 349: 254; Strasser et al. (1991) *Cell* 67: 889).

The bcl-2 protein is a 26 kD membrane-associated cytoplasmic protein (Tsujimoto et al. (1987) *Oncogene* 2: 3; U.S. Pat. Nos. 5,202,429 and 5,015,568; Chen-Levy (1989) op.cit; Hockenberry (1990) op.cit). Unlike many other proto-oncogene products, the bcl-2 protein apparently functions, at least in part, by enhancing the survival of hematopoietic cells of T and B origins rather than by directly promoting proliferation of these cell types (Vaux et al. (1988) *Nature* 335: 440; Tsujimoto Y (1989) *Proc. Natl. Acad. Sci.* (U.S.A.) 86: 1958; Tsujimoto Y (1989) *Oncogene* 4: 1331; Reed et al. (1989) *Oncogene* 4: 1123; Nunez et al. (1989) *Proc. Natl. Acad. Sci.* (U.S.A.) 86: 4589; Nunez et al. (1990) *J. Immunol.* 144: 3602; Reed et al. (1990) *Proc. Natl. Acad. Sci.* (U.S.A.) 87: 3660; Alnemri et al. (1992) *Proc. Natl. Acad. Sci.* (U.S.A.) 89: 7295). The capacity of bcl-2 to enhance cell survival is related to its ability to inhibit apoptosis initiated by several factors, such as cytokine deprivation, radiation exposure, glucocorticoid treatment, and administration of anti-CD-3 antibody (Nunez et al. (1990) op.cit; Hockenberry et al. (1990) op.cit; Vaux et al. (1988) op.cit; Alnemri et al. (1992) *Cancer Res.* 52: 491; Sentman et al. (1991) *Cell* 67: 879; Strasser et al. (1991) op.cit). Upregulation of bcl-2 expression also inhibits apoptosis of EBV-infected B-cell lines (Henderson et al. (1991) *Cell* 65: 1107). The expression of bcl-2 has also been shown to block apoptosis resulting from expression of the positive cell growth regulatory proto-oncogene, c-myc, in the absence of serum or growth factors (Wagner et al (1993) *Mol. Cell. Biol.* 13: 2432). However, the precise mechanism(s) by which bcl-2 is able to inhibit apoptosis is not yet fully defined.

R-ras

The mammalian genome contains at least three transcribed ras proto-oncogenes, H-ras, K-ras, and N-ras, which each encode highly related 21 kD polypeptides (p21) of 188–189 amino acids. The yeast *Saccharomyces cerevisiae* has two ras genes, designated RAS1 and RAS2. These ras genes encode membrane-localized cytoplasmic proteins which bind GTP and have intrinsic GTPase activity, and function in signal transduction pathways regulating cell proliferation. Certain characteristic mutations in these ras genes have been associated with neoplastic and preneoplastic conditions, and several mutant ras alleles can confer a dominant transformed phenotype on cells transfected with these alleles.

Probes derived from mammalian ras gene sequences have been used to identify related cDNA and genomic clones by screening using low-stringency hybridization. Many of the clones identified by this method encode small (approximately 21 kD) guanine-nucleotide binding proteins. These genes are generally termed "ras-related genes", and comprise several distinct genes having differing degrees of sequence identity to the ras genes (Garrett et al. (1989) *J. Biol. Chem.* 264: 10). One of the ras-related genes is the R-ras gene identified by low-stringency hybridization using a v-H-ras gene probe (Lowe et al. (1987) *Cell* 48: 137; Lowe D G and Goeddel D V (1987) *Mol. Cell. Biol.* 7: 2845). The predicted human R-ras gene product is 218 amino acids and has a calculated molecular weight of 23.4 kD (designated p23). The R-ras p23 protein has an amino-terminal extension of 26 amino acids relative to the H-, K-, and N-ras p21 proteins. The deduced amino acid sequence of human R-ras has approximately 55 percent sequence identity in the region of overlap with human H-ras p21, with invariantly conserved regions including the predicted guanine-nucleotide binding site and the lipid atachment sequence Cys-A-A-X, where A is an aliphatic amino acid and X is the carboxyl-terminal amino acid.

R-ras p23 appears as a membrane-localized GTPase and may interact with a GTPase-activating protein (GAP) species (Garrett et al. (1989) op.cit); these interactions may be affected by the presence of certain lipid species (Tsai et al. (1989) *Mol. Cell. Biol.* 9: 5260). Although ras p21 proteins are known to be integral components of signal transduction mechanisms leading to control of cell proliferation, no published reports have conclusively identified a biochemical function for R-ras.

Cell Proliferation Control and Neoplasia

Many pathological conditions result, at least in part, from aberrant control of cell proliferation, differentiation, and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

The precise molecular pathways and secondary changes leading to malignant transformation for many cell types are not clear. However, the characteristic translocation of the apoptosis-associated bcl-2 gene to the immunoglobulin heavy chain locus t(14;18) in more than 80 percent of human follicular B cell lymphomas and 20 percent of diffuse lymphomas and the neoplastic follicular lymphoproliferation present in transgenic mice expressing high levels of bcl-2 indicates that the bcl-2 gene likely is causally involved in neoplastic diseases and other pathological conditions resulting from abnormal cell proliferation, differentiation, and/or apoptosis. Thus, it might be desirable to identify agents which can modify the activity(ies) of the bcl-2 protein so as to modulate cell proliferation, differentiation, and/or apoptosis for therapeutic or prophylactic benefit. Further, such agents can serve as commercial research reagents for control of cell proliferation, differentiation, and/or apoptosis in experimental applications, and/or for controlled proliferation and differentiation of predetermined hematopoietic stem cell populations in vitro, in ex vivo therapy, or in vivo.

Despite progress in developing a more defined model of the molecular mechanisms underlying the transformed phenotype and neoplasia, few significant therapeutic methods applicable to treating cancer beyond conventional chemotherapy have resulted. Such bcl-2 modulating agents can provide novel chemotherapeutic agents for treatment of neoplasia, lymphoproliferative conditions, arthritis, inflammation, autoimmune diseases, and the like. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for modulating the activity of the bcl-2 gene product, p23, and thereby modulating cell proliferation and apoptosis, especially of cells derived from the hematopoietic lineage (e.g., lymphocytes). Such modulation of bcl-2 activity can provide a means to inhibit neoplastic conditions, especially lymphomas, leukemias, and the like, and a means to modulate an immune response and inflammatory response. Apoptosis has also been linked to Alzheimer's disease and other neurodegenerative diseases.

The present invention provides compositions and methods for screening for agents which are modulators of bcl-2 function and can modulate bcl-2-mediated apoptosis and/or modulate neoplastic and immune conditions dependent upon bcl-2 function.

The present invention provides a composition comprising a substantially pure protein complex comprising a R-ras polypeptide and a bcl-2 polypeptide. The invention also provides fragments of R-ras and bcl-2 which retain the ability to bind, forming a R-ras:bcl-2 complex under physiological conditions. In one variation, the R-ras polypeptide comprises the carboxyl-terminal 60 amino acids of human R-ras.

Definitions

Figure 1:
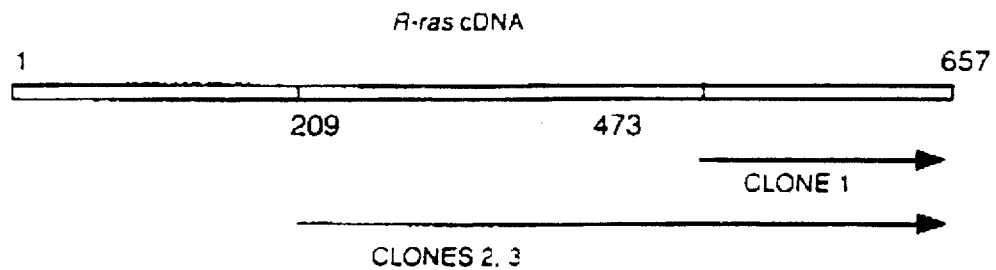
FIG. 1 shows schematically the relative positions of R-ras clones 1, 2, and 3 as compared to the full-length human R-ras cDNA; clone 1 encode amino acids 158–218, clones 2 and 3 encode amino acids 71–218.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length R-ras or bcl-2 cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity", is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human bcl-2 or R-ras cDNA sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "native protein" and "full-length protein" as used herein refers to a polypeptide corresponding to the deduced amino acid sequence of a human bcl-2 cDNA or R-ras cDNA or corresponding to the deduced amino acid sequence of a cognate full-length bcl-2 or R-ras cDNA from a nonhuman mammal.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., a human bcl-2 or R-ras cDNA sequence). Fragments typically are at least 14 amino acids long, preferably at least 20 amino acids long, usually at least 50 amino acids long or longer, and span the portion of the polypeptide required for intermolecular binding of bcl-2 to R-ras.

The term "analog" as used herein refers to polypeptides which are comprised of a segment of at least 25 amino acids that has substantial identity to a portion of the deduced amino acid sequence of human bcl-2 or R-ras cDNAs, and which has the property of binding to R-ras or bcl-2 protein, respectively, to form a detectable bcl-2:R-ras complex.

The term "polypeptide" is used herein as a generic term to refer to native protein, fragments, or analogs of bcl-2 or R-ras. Hence, native R-ras, fragments of R-ras, and analogs of R-ras are species of the R-ras polypeptide genus.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antineoplastics and/or inhibitors of bcl-2 function by inclusion in screening assays described hereinbelow.

The term "bcl-2 antagonist" is used herein to refer to agents which inhibit bcl-2 activity and can produce a cell phenotype characteristic of cells having reduced or undetectable expression of bcl-2; bcl-2 antagonists typically will enhance apoptosis. In contradistinction, bcl-2 agonists will enhance bcl-2 activity and will usually reduce apoptosis.

The term "antineoplastic agent" is used herein to refer to agents that have the functional property of inhibiting a development or progression of a neoplasm in a human, particularly a lymphocytic leukemia, lymphoma, or preleukemic condition.

The term "candidate antineoplastic agent" is used herein to refer to an agent which is identified by one or more screening method(s) of the invention as a putative antineoplastic agent. Some candidate antineoplastic agents may have therapeutic potential as anticancer drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied BioSystems oligonucleotide synthesizer according to specifications provided by the manufacturer.

Identification of Polypeptides Which Interact with bcl-2

A yeast two-hybrid system can be used to identify proteins which can undergo intermolecular binding to form a polypeptide complex under physiological conditions (Chien et al. (1991) Proc. Natl. Acad. Sci. (U.S.A.) 88: 9578, incorporated herein by reference). Expression vectors are constructed to encode two hybrid proteins; one hybrid consists of the DNA-binding domain of the yeast transcriptional activator protein, GAL4, fused to a predetermined polypeptide sequence and the other hybrid consists of the GAL4 activation domain fused to polypeptide sequences encoded by a library of polynucleotide sequences (e.g., a mammalian cDNA library). The vectors are inserted into yeast by conventional methods (Chien et al. (1991) op.cit). Intermolecular interaction between the predetermined polypeptide and a polypeptide encoded by one of the library plasmids leads to transcriptional activation of a reporter gene containing a cis-linked binding site for GAL4.

In a preferred embodiment, the human bcl-2 cDNA (Hockenberry et al. (1990) op.cit, incorporated by reference) encodes the predetermined polypeptide sequence fused to form a first hybrid protein, and a human HeLa cDNA library is fused to form the library of second hybrid proteins. A GAL4-dependent β-galactosidase gene is used as a reporter. Yeast harboring the reporter gene and vectors encoding the first and second hybrids are plated and yeast colonies expressing detectable (i.e., significantly greater than control) levels of β-galactosidase are selected. The sequence(s) of the second hybrid polypeptide library member is determined by nucleic acid sequencing. Polypeptide sequences which specifically interact with bcl-2 can be thereby identified as putative bcl-2 modulators.

R-ras:bcl-2 Intermolecular Association

A basis of the present invention is the surprising finding that the R-ras p23 protein forms a complex with the bcl-2 protein under physiological conditions. Moreover, only the carboxyl-terminal portion of R-ras (e.g., the 60 carboxyl-terminal amino acids) is required for generating an intermolecular association with bcl-2. This finding indicates that the R-ras protein serves as a modulator of bcl-2 function, and vice versa. Such functional modulation can serve to couple a signal transduction pathway (via R-ras) to an apoptosis regulatory protein (i.e., bcl-2). This finding indicates that R-ras p23 can be a component of a signal transduction pathway that mediates external signals involved in the induction of bcl-2-mediated apoptosis.

Assays for detecting the ability of agents to inhibit the binding of R-ras to bcl-2 provide for facile high-throughput screening of agent banks (e.g., compound libraries, peptide libraries, and the like) to identify bcl-2 antagonists or agonists. Such bcl-2 antagonists and agonists may modulate bcl-2 activity and thereby modulate apoptosis.

Fragments and analogs of R-ras, especially peptidomimetics (infra), may provide competitive or non-competitive inhibitors of bcl-2:R-ras complex formation and thereby serve as effective bcl-2 antagonists or agonists and may modulate bcl-2 activity and thereby modulate apoptosis.

Administration of an efficacious dose of an agent capable of specifically inhibiting bcl-2:R-ras complex formation to a patient can be used as a therapeutic or prophylactic method for treating pathological conditions (e.g., cancer, inflammation, lymphoproliferative diseases, autoimmune disease, and the like) which are effectively treated by modulating bcl-2 activity and apoptosis.

Production of bcl-2 and R-ras Polypeptides

The nucleotide and amino acid sequences of mammalian (e.g., human, murine) bcl-2 and R-ras are available from GenBank and are published (e.g., U.S. Pat. No. 5,202,429 and Lowe et al. (1987) op.cit, incorporated herein by reference) thereby enabling those of skill in the art to produce polypeptides corresponding to all or part of the full-length polypeptide sequences. Such polypeptides may be produced in prokaryotic or eukaryotic host cells by expression of polynucleotides encoding bcl-2 or R-ras, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology*, Volume 152, *Guide to Molecular Cloning Techniques* (1987), Academic Press, Inc., San Diego, Calif.

Fragments or analogs of bcl-2 or R-ras may be prepared by those of skill in the art. Preferred amino- and carboxy-termini of fragments or analogs occur near boundaries of functional domains. For example, but not for limitation, such functional domains include: (1) domains conferring the property of binding to form a R-ras:bcl-2 complex, (2) domains conferring the property of membrane localization, and (3) domains conferring the property of modulating apoptosis of cells when expressed at sufficient levels in such cells.

One method by which structural and functional domains may be identified is by comparison of the nucleotide and/or amino acid sequence data to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the R-ras and bcl-2 sequences. For example but not limitation, the carboxyl-terminal 60 amino acids of the human R-ras comprises a functional domain capable of mediating complex formation with bcl-2.

Fragments or analogs comprising substantially one or more functional domain may be fused to heterologous polypeptide sequences, wherein the resultant fusion protein exhibits the functional property(ies) conferred by the fragment. Alternatively, polypeptides wherein one or more functional domain have been deleted will exhibit a loss of the property normally conferred by the missing fragment.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of R-ras and bcl-2 can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to a native R-ras or bcl-2 protein. However, analogs must comprise a segment of 25 amino acids that has substantial identity to a portion of the native protein amino acid sequence. Preferred amino acid substitutions are those which: (1) reduce susceptibility to proteolysis, (2) reduce susceptibility to oxidation, (3) alter binding affinity for forming R-ras:bcl-2 complexes, and (4) confer or modify other physicochemical or functional properties of such analogs. Analogs include various muteins of a R-ras or bcl-2 sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts.

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Peptidomimetics

It may be advantageous to employ a peptide analog of R-ras or bcl-2, or a portion thereof, as a pharmaceutical agent or as a commercial research reagent. For example, a peptide analog of R-ras having high affinity for binding bcl-2 may be used as a competitive inhibitor of R-ras:bcl-2 complex formation by competing with native R-ras for binding to bcl-2.

In addition to polypeptides consisting only of naturally-occuring amino acids, peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human R-ras, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R. G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., are not contact points in R-ras:bcl-2 complexes) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

Methods of Identifying Novel Antineoplastic and Immunomodulatory Agents

A basis of the present invention is the experimental finding that R-ras and bcl-2 polypeptides form a high affinity intermolecular complex under physiological conditions, and that R-ras:bcl-2 complexes are co-immunoprecipitated from HeLa and HL-60 cell extracts. On the basis of these findings, the formation of R-ras:bcl-2 complexes is identified as a target for agents capable of modulating bcl-2-dependent apoptosis; and as a target for novel chemotherapeutic or chemopreventative antineoplastic and immunomodulatory agents. For example, agents which alter R-ras:bcl-2 interactions in neoplastic and/or preneoplastic cells may be developed as potential human therapeutic drugs. Candidate antineoplastic agents may be identified by their ability to inhibit R-ras:bcl-2 complex formation in vitro and/or in vivo and/or inhibit bcl-2 protein function in vivo (e.g., inhibit the ability of bcl-2 protein to specifically block apoptosis).

Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Agents which enhance bcl-2-dependent apoptosis may serve as immunomodulatory agents, for example, to attenuate an inflammatory reaction, graft-versus-host reaction, or autoimmune condition, neurodegenerative diseases, neoplasia, and the like.

R-ras:bcl-2 Binding Assays

One category of assay in which bcl-2-modulating agents (e.g., candidate antineoplastic agents) may be identified is a binding inhibition assay, wherein agents are individually (or in pools) evaluated for their ability to inhibit formation of a binding complex comprising a R-ras polypeptide bound to a bcl-2 polypeptide under aqueous binding conditions in which R-ras:bcl-2 binding occurs in the absence of the agent (see Experimental Examples, infra). bcl-2-modulating agents (e.g., candidate antineoplastic agents) can be identified by screening for agents which interfere with the formation of functional R-ras:bcl-2 complexes. Agents which inhibit binding of R-ras polypeptides to bcl-2 polypeptides are identified as bcl-2-modulating agents (e.g., candidate antineoplastic agents).

The screening assays of the present invention may utilize isolated or purified forms of the assay components (bcl-2 polypeptides and R-ras polypeptides). This refers to polypeptides of the present invention which have been separated from their native environment (e.g., a cytoplasmic or nuclear fraction of a cell, yeast protoplasm, or by recombinant production), to at least about 10–50% purity. A substantially pure composition includes such polypeptide(s) or complexes that are approaching homogeneity, i.e., about 80–90% pure, preferably 95–99% pure. Preferred embodiments include binding assays which use R-ras and bcl-2 polypeptides which are produced by recombinant methods or chemically synthesized.

Additional preferred embodiments comprise R-ras and/or bcl-2 analogs that have superior stabilities as experimental reagents. For example, preferred analogs may be resistant to degradation by proteolytic activities present in the binding reaction(s), and/or may be resistant to oxidative inactivation. Such analogs may include amino acid substitutions which remove proteolytic cleavage sites and/or replace residues responsible for oxidative inactivation (e.g., methionine, cysteine). However, the analogs must be functional in at least the control binding assay(s); therefore, analogs comprising amino acid substitutions which destroy or significantly degrade the functional utility of the analog in the binding assay are not employed for such assays.

These methods of screening may involve labelling a R-ras and/or bcl-2 polypeptide with any of a myriad of suitable markers, including radiolabels (e.g., $^{125}$I or $^{32}$P), various fluorescent labels and enzymes, (e.g., glutathione-S-transferase, luciferase, and β-galactosidase). If desired for basic binding assays, the target polypeptide (R-ras or bcl-2) may be immobilized by standard techniques. For example but not for limitation, such immobilization may be effected by linkage to a solid support, such as a chromatographic matrix, or by binding to a charged surface, such as a Nylon 66 membrane.

Binding assays generally take one of two forms: immobilized R-ras polypeptide(s) can be used to bind labeled bcl-2 polypeptide(s), or conversely, immobilized bcl-2 polypeptide(s) can be used to bind labeled R-ras polypeptides. In each case, the labeled polypeptide is contacted with the immobilized polypeptide under aqueous conditions that permit specific binding of the polypeptides(s) to form a R-ras:bcl-2 complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of R-ras polypeptide(s) to bcl-2 polypeptides occurs in the control reaction(s). Conditions that do not permit specific binding in control reactions (no agent included) are not suitable for use in inding assays.

Preferably, at least one polypeptide species is labeled with a detectable marker. Suitable labeling includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a R-ras or bcl-2 polypeptide may be used in combination with an accessory protein (e.g., a protein which forms a complex with the polypeptide in vivo), it is preferred that different labels are used for each polypeptide species, so that binding of individual and/or heterodimeric and/or multimeric complexes can be distinguished. For example but not limitation, a R-ras polypeptide may be labeled with fluorescein and an accessory polypeptide may be labeled with a fluorescent marker that fluorescesces with either a different excitation wavelength or emission wavelength, or both. Alternatively, double-label scintillation counting may be used, wherein a R-ras polypeptide is labeled with one isotope (e.g., $^{3}$H) and a second polypeptide species is labeled with a different isotope (e.g., $^{14}$C) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound R-ras:bcl-2 complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles*, (1984) Creighton (ed.), W. H. Freeman and Company, New York).

Specific binding of labeled R-ras or bcl-2 polypeptide to immobilized bcl-2 or R-ras polypeptide, respectively, is determined by including unlabeled competitor protein(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a R-ras polypeptide and a bcl-2 polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci.* (U.S.A.) 83: 5889, which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a R-ras polypeptide to a bcl-2 polypeptide. Agents that inhibit binding relative to the control reaction(s) are thereby identified as bcl-2-modulating agents and/or candidate antineoplastic agents and/or candidate immunomodulatory agents.

In one variation, GTPase activity and/or GDP- or GTP-binding activity of R-ras is measured as the assay endpoint. The ability of bcl-2 polypeptide to modulate one or more of these guanine nucleotide activities of R-ras serves as the basis for the screening assay. Test compounds which modulate the activity of bcl-2 to modulate a R-ras guanine nucleotide activities are thereby identified as bcl-2 modulators and R-ras modulators.

Yeast Two-Hybrid Screening Assays

Yeast comprising (1) an expression cassette encoding a GAL4 DNA binding domain (or GAL4 activator domain) fused to a binding fragment of bcl-2 capable of binding to a R-ras polypeptide, (2) an expression cassette encoding a GAL4 DNA activator domain (or GAL4 binding domain, respectively) fused to a binding fragment of R-ras capable of binding to a bcl-2 polypeptide, and (3) a reporter gene (e.g., β-galactosidase) comprising a cis-linked GAL4 transcriptional response element can be used for agent screening. Such yeast are incubated with a test agent and expression of the reporter gene (e.g., β-galactosidase) is determined; the capacity of the agent to inhibit expression of the reporter gene as compared to a control culture identifies the agent as a candidate bcl-2-modulatory agent or R-ras modulatory agent.

Methods for Rational Drug Design

R-ras and bcl-2 polypeptides, especially those portions which form direct contacts in R-ras:bcl-2 complexes, can be used for rational drug design of candidate bcl-2-modulating agents (e.g., antineoplastics and immunomodulators). The substantially purified R-ras:bcl-2 complexes and the identification of R-ras as a docking partner for bcl-2 as provided herein permits production of substantially pure R-ras:bcl-2 polypeptide complexes and computational models which can be used for protein X-ray crystallography or other structure analysis methods, such as the DOCK program (Kuntz et al. (1982) *J. Mol. Biol.* 161: 269; Kuntz I D (1992) *Science* 257: 1078) and variants thereof. Potential therapeutic drugs may be designed rationally on the basis of structural information thus provided. In one embodiment, such drugs are designed to prevent formation of a R-ras protein:bcl-2 protein complex.

Thus, the present invention may be used to design drugs, including drugs with a capacity to inhibit binding of R-ras to bcl-2.

The design of compounds that interact preferentially with a R-ras or bcl-2 polypeptide or R-ras:bcl-2 complex can be developed using computer analysis of three-dimensional structures. A set of molecular coordinates can be determined using: (1) crystallographic data, (2) data obtained by other physical methods, (3) data generated by computerized structure prediction programs operating on the deduced amino acid sequence data, or, preferably, a combination of these data. Examples of physical methods that may be used to define structure are, for example, two-dimensional homonuclear correlated spectroscopy (COSY). For those skilled in the art with one-dimensional NMR spectroscopy, COSY provides the kind of information available from a single-frequency decoupling experiment (e.g., which spins are scalar coupled to one another). In a COSY plot, the 1D spectrum lies along the diagonal, and the off-diagonal elements are present at the intersection of chemical shifts of groups that are J coupled. The "fingerprint" region contains ($^1H^N$, $^1H^\alpha$) cross-peaks from the peptide backbone. The degree of resolution of the "fingerprint" region of the COSY map obtained in $H_2O$ is a good predictor of the success of sequence-specific assignments to be obtained without recourse to isotopic labeling.

Transferred nuclear Overhauser effect (TRNOE) spectra ($^1H$ NMR) relies on different 2D NOE spectra, and, in essence, looks at the conformation of the ligand just after it has dissociated from the protein. The use of TRNOE presumes, however, that the bound and free ligands are in fast exchange on the chemical shift time scale, which translates to a ligand $K_D$ greater than or equal to about $1 \times 10^{-4}$M. TRNOE methods are useful to crosscheck and augment the distance information obtained by other approaches.

It is not intended that the present invention be limited by the particular method used to obtain structural information. Furthermore, it is not intended that the present invention be limited to a search for any one type of drug; one or more of the molecules may be naturally-occurring or may be synthetic, or may be a chemically-modified form of a naturally-occurring molecule.

In some embodiments, it is desirable to compare the structure of R-ras or bcl-2 protein(s) to the structure(s) of other proteins. This will aid in the identification of and selection of drugs that either selectively affect R-ras or bcl-2, or have a broad-spectrum effect on more than one species of related polypeptide (e.g., other ras-related proteins).

EXPERIMENTAL EXAMPLES

Identification of R-ras as a bcl-2-binding Protein

The cDNA encoding human bcl-2 (Hockenberry et al. (1990) op.cit) was fused to the GAL4 binding domain in the pGBT8 plasmid, which is the pMA424 plasmid of Chien et al. (1991) op.cit. modified by the insertion of the sequence 5'-CCGGGGATCCCCATGGCTAGCCATATG-3' between the Eco RI and Sal I unique sites, and transformed into the yeast strain YGH1. The YGH1 strain carrying the GAL4-bcl-2 plasmid was transformed with a HeLa cDNA library fused to the GAL4 activation domain in the pGAD plasmid (Chien et al. (1991) op.cit). When a cDNA encodes a protein that interacts with the bcl-2 protein, the YGH1 strain is expected to grow in the absence of histidine and produce β-galactosidase. Twenty of the $2 \times 10^6$ transformants screened grew in the absence of histidine and had β-galactosidase activity. The plasmids recovered from these 20 yeast strains were used to retransform the original YGH1+bcl-2 strain. All the plasmids conferred the ability to grow in the absence of histidine and to produce β-galactosidase. Three of the plasmids contained cDNAs encoding human R-ras. FIG. 1 shows the portions of R-ras encoded in each of these clones.

The YGH1 yeast strain was transformed with clone 1 and either bcl-2 cDNA or p53 cDNA, fused to the GAL4 binding domain. Transformants were tested for the ability to grow in the absence of histidine, which indicates interaction between proteins fused to the GAL4 activation domain (R-ras) and the GAL4 DNA-binding domain (bcl-2 or p53). The plates were incubated for 4 days at 30 degrees C. The yeast transformed with the bcl-2 cDNA grew in the absence of histidine and expressed β-galactosidase, whereas the yeast transformed with the p53 cDNA did not, demonstrating specificity of the interaction between bcl-2 and R-ras.

Full-Length bcl-2 Protein Required to Associate with R-ras

Figure 2:
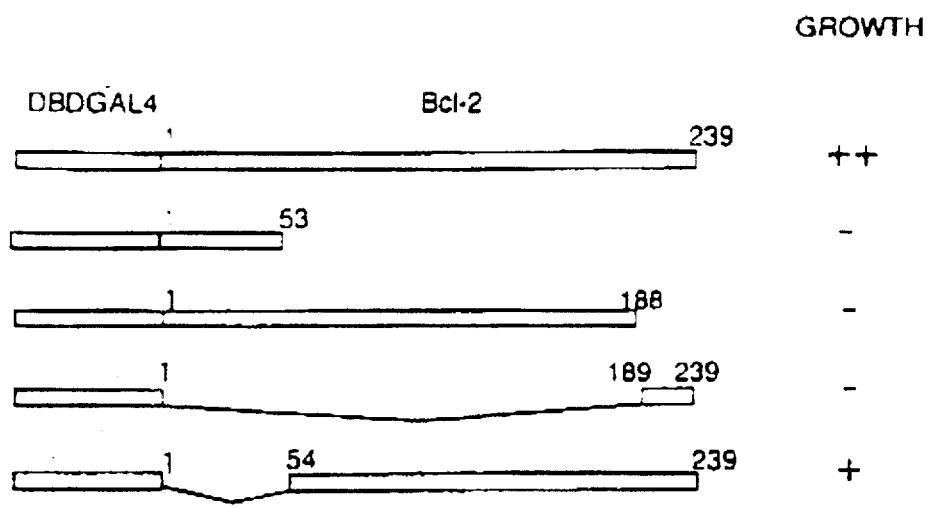
FIG. 2 shows schematic maps of the bcl-2 deletions tested for interaction with R-ras clone 1. Relative growth is indicated as follws: ++, normal growth; +, slow growth; −, no growth.
Figure 3:
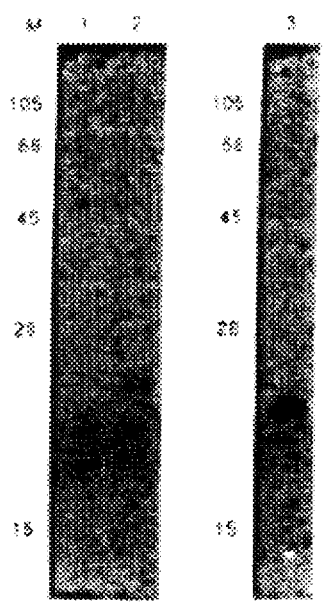
FIG. 3 shows a nitrocellulose blot of a SDS-PAGE of GTP-binding proteins which co-immunoprecipitate with anti-bcl-2 antibody.

Deletions of the bcl-2 cDNA were made using standard molecular biology techniques and verified by sequencing. The deletion constructs are shown schematically in FIG. 2. The bcl-2 deletion constructs were fused to the GAL4 DNA-binding domain (DBDGAL4) and co-transformed into YGH1 with R-ras clone 1 fused to the GAL4 activation domain. The transformed yeast was allowed to grow in the presence of histidine and then was streaked out to test for growth in the absence of histidine. Histidine-independent growth was best (normal) with the full-length bcl-2 clone.

mM $MgCl_2$. An approximately 23 kD GTP-binding protein co-precipitates with human bcl-2 as is shown in FIG. 3, lane 2; this protein is putatively identified as human R-ras.

bcl-2 Co-immunoprecipitates with R-ras p23

Figure 4:
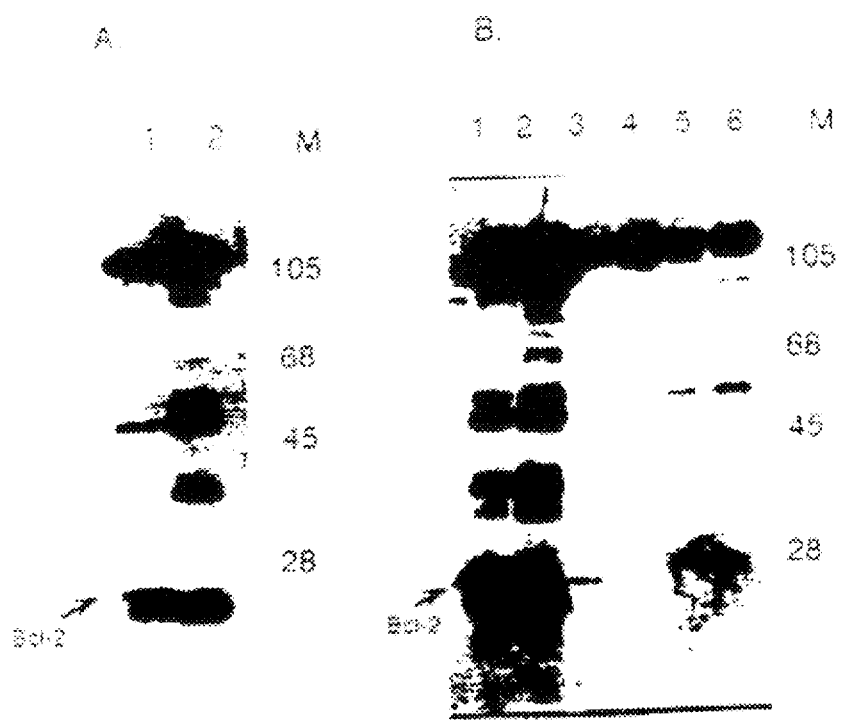
FIG. 4 shows a western blot of proteins that co-immunoprecipitate with anti-R-ras antibody; western blot was stained with anti-bcl-2 antibody.

HL60 cells were washed twice with ice-cold PBS. Cells were lysed and the P100 membrane fraction was isolated as previously described (Lowe D G and Goeddel D V (1987) op.cit). One milligram of total protein was immunoprecipitated with either a monoclonal antibody against human bcl-2 (DAKO), rabbit polyclonal antibodies against human R-ras p23 (Lowe D G and Goeddel D V (1987) op.cit), or monoclonal antibody PAb416 against T antigen. Since the bcl-2 protein comigrates with the IgG light chain during electrophoresis, the above antibodies with no lysate was used as a control for a western blot (FIG. 4, lanes 2, 4, and 6). The immunoprecipitates were washed three times with 50 mM Tris-HCl (pH 7.5), 200 mM NaCl, 0.1% NP-40. The proteins were resolved on a 11.5% SDS-PAGE, transferred to a nitrocellulose filter and probed with anti-bcl-2 antibody. The secondary antibody was peroxidase-conjugated goat antimouse IgG, Fcγ fragment-specific (Jackson ImmunoResearch Laboratories). The ECL system (Amersham) was used to develop the blot. In FIG. 4, lanes 1 and 2 contain anti-bcl-2 immunoprecipitates; lanes 3 and 4 contain anti-R-ras immunoprecipitates; and lanes 5 and 6 contain anti-T antigen immunoprecipitates—lanes 1, 3, and 5 contain HL60 membrane fraction and lane 2, 4, and 6 contain lysis buffer.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CCGGGATCC CCATGGCTAG CCATATG 27

A 23 kD GTP-Binding Protein Co-Precipitates with bcl-2

HeLa cells were washed twice with ice-cold PBS and lysed in 10 mM $NaPO_4$ (pH 7.4), 150 mM NaCl, 5 mM EDTA, 1% Triton X-100. The lysate was centrifuged at 5,000 rpm in a 4 degree C. Eppendorf microfuge and the pellet discarded. One milligram of total protein was immunoprecipitated with anti-p53 monoclonal antibody, PAb421 (FIG. 3, lane 1) or with a monoclonal antibody to human bcl-2 (DAKO) (FIG. 3, lane 2). As a positive control, bacterially produced human N-ras protein was loaded (FIG. 3, lane 3). The proteins were resolved on a 11.5% SDS-PAGE, transferred to a nitrocellulose filter, and probed with $^{32}P$-α-GTP as described (Lerosey et al. (1991) J. Biol. Chem. 266: 4315), except the washing buffer contained 10

We claim:

1. A method of screening for candidate bcl-2 modulating agents, comprising:

performing a heterodimerization assay which includes combining substantially purified full length R-ras polypeptide with a substantially purified full length bcl-2 polypeptide and an agent; and determining whether the agent inhibits the heterodimerization.

2. A method for screening for candidate bcl-2-modulating agents, comprising:

performing a heterodimerization assay which includes combining a substantially purified R-ras polypeptide, said R-ras polypeptide having at least 60 C-terminal domain amino acids of a naturally occurring R-ras polypeptide, with a substantially purified full length bcl-2 polypeptide, and an agent; and determining whether the agent inhibits the heterodimerization.

3. A method of claim 1, or claim 2 wherein the heterodimerization assay comprises an in vitro binding reaction.

4. A method of claim 1, or claim 2 wherein the heterodimerization assay comprises a two-hybrid assay in yeast.

5. A method of claim 1 or claim 2 wherein the two-hybrid assay comprises a human R-ras polypeptide sequence fused to a GAL4 protein and a human bcl-2 polypeptide sequence fused to a GAL4 protein.

6. A method of claim 3, wherein a R-ras or bcl-2 polypeptide is immobilized.

7. A method for altering apoptosis of an isolated cell, comprising administering to said cell an agent that inhibits R-ras:bcl-2 heterodimerization formation as described in claim 1 or claim 2.

8. A method of claim 7, wherein said cell is derived from the hematopoietic lineage.

9. A method of claim 7, wherein the cell is a neoplastic cell.

10. A method of claim 8, wherein the cell is a leukocyte.

* * * * *